US005602262A

United States Patent [19]
Wirth

[11] Patent Number: 5,602,262

[45] Date of Patent: Feb. 11, 1997

[54] PROCESS FOR THE PREPARATION OF 2-DEOXY-2,2-DIFLUORO-β-D-RIBO-PENTOPYRANOSE

[75] Inventor: David D. Wirth, Lafayette, Ind.

[73] Assignee: Eli Lilly and Company, Indianapolis, Ind.

[21] Appl. No.: 383,047

[22] Filed: Feb. 3, 1995

[51] Int. Cl.$^6$ .................. C07D 309/10; C07D 317/16
[52] U.S. Cl. .................. 549/417; 549/418; 549/423; 549/454; 549/455
[58] Field of Search .................. 549/417, 418, 549/423, 454, 455

[56] References Cited

U.S. PATENT DOCUMENTS 4,954,623   9/1990   Nagarajan .................. 536/127

OTHER PUBLICATIONS

Chou, T. S., et al., *Synthesis*, 6, pp. 565–570 (1992).
Hertel, L. W., et al., *J. Org. Chem.*, 53, pp. 2406–2409 (1988).
Yang, Z., et al., *J. Org. Chem.*, 53, pp. 1037–1041, (1991).
Hanzawa, Y., et al., *Tetrahedron Letters*, 28, No. 6, pp. 659–662 (1987).
Seyferth, D., et al., *J. Am. Chem. Soc.*, 105, pp. 4634–4639 (1983).

*Primary Examiner*—Ba K. Trinh
*Attorney, Agent, or Firm*—Margaret M. Brumm; David E. Boone

[57] ABSTRACT

A process for producing intermediate compounds 2-deoxy 2,2-difluoro-β-D-ribo-pentopyranose (III) from 3,3-difluoro-4,5,6-O-trihydroxy-5,6-O-(1-ethylpropylidene)hexene (I). The process of preparing intermediate compound (I) involves reacting D-glyceraldehyde pentanide with an organometallic complex of 3-bromo-3,3-difluoropropene. The process of preparing intermediate compound (III) involves ozonolysis and then hydrolysis. The intermediate compounds (I) and (III) are used in the preparation of 2'-deoxy-2',2'-difluorocytidine which is an antiviral agent.

19 Claims, No Drawings

PROCESS FOR THE PREPARATION OF 2-DEOXY-2,2-DIFLUORO-β-D-RIBO-PENTOPYRANOSE

BACKGROUND OF THE INVENTION

The present invention relates to the preparation of 2-deoxy-2,2-difluoro-β-D-ribo-pentopyranose (III) from 3,3-difluoro-4,5,6-trihydroxy-5,6-O-(1-ethylpropylidene)hexene (I), wherein a pentopyranose isomer (IIIA) is produced preferentially. The hexene (I) is prepared by a novel process from glyceraldehyde pentanide. The pentopyranose isomer (IIIA) is an intermediate to 2'-deoxy-2',2'-difluorocytidine, a known antiviral agent.

Hanzawa, et al., *Tetrahedron Letters*, 28, 659–662 (1987) describe the reaction of bromodifluoromethylacetylene compounds with various aldehydes. The reaction was conducted at 0° C. and mercurous chloride was necessary to activate the zinc. There was no need for a protective atmosphere. The yields of the acetylenic difluoro acetonides were in the 50 to 78% range. A 2,2-difluoro ribose was produced from an intermediate difluoro acetonide using a complex series of reactions. There is no indication of any preference for any isomeric product.

Yang, et al., *J. Organic Chem.*, 56, 1037–1041 (1991) describe the general preparation of α,α-difluorohomoallylic alcohols by the reaction of an aldehyde, zinc and 3-bromo-3,3-difluoropropene. None of the reactions involved protected glyceraldehydes or other chiral aldehydes so there is no indication of any isomeric preference. The reference does show that various metals can be used to form the complex, particularly cadmium and tin. Seyferth, et al., *J. Am. Chem.*, 105, 4634–4639 (1983) shows the use of a lithium complex in general reactions with an aldehyde, but not with protected glyceraldehydes or chiral aldehydes. There is no showing of preferential production of an isomer. Hertel, et al., *J. Org. Chem.*, 53, 2406–2409 (1988) disclose the preparation of pentopyranose isomer (IIIA) from difluoroacetates, while Nagarajan's patent (U.S. Pat. No. 4,954,623) produces it by degrading a nucleoside. Importantly, however, Nagarajan's patent also discloses use of difluorodeoxyribose IIIA to prepare the ribofurano-1,4-lactone intermediate which is used in the Hertel and Chou papers (Chou, et al., *Synthesis*, 565–570 (1992)) to prepare 2'-deoxy-2',2'-difluorocytidine. In the Hertel and Nagarajan preparations of IIIA, its xylo isomer IIIB is not present and therefore separation of the two isomers is not shown. Hanzawa, et al., *Tet. Lett.*, 28, 659–662 (1987) show a general reaction to produce a difluorodeoxyribose which was not suitable for nucleoside formation. Triacetoxydifluoro-deoxy pyranosylribose was isolated, not the unprotected form needed to form 2'-deoxy-2',2'-difluorocytidine.

It is therefore an object of the present invention to provide a novel process for the preparation of a ribo-pentopyranose intermediate to the preparation of 2'-deoxy-2',2'-difluorocytidine. Further, it is an object of the present invention to provide a novel reaction to produce 3,3-difluoro-4,5,6-trihydroxy-5,6-O-(1-ethylpropylidene)hexene (I), particularly with a significant excess of the erythro isomer. These and other objects will become increasingly apparent by reference to the following description.

SUMMARY OF THE INVENTION

The present invention relates to a process for the preparation of D-3,3-difluoro-4,5,6-trihydroxy-5,6-O(1-ethylpropylidene)hexene (I) the improvement which comprises: reacting in a reaction mixture an organometallic complex of 3-bromo-3,3-difluoropropene with D-glyceraldehyde pentanide in a non-reactive organic solvent until the hexene (I) is formed in the reaction mixture. In this reaction, there is a substantial excess of the erythro isomer hexene (IA).

The present invention also relates to a process for the preparation of 2-deoxy-2,2-difluoro-β-D-ribo-pentopyranose (III) which comprises: reacting D-3,3-difluoro-4,5,6-trihydroxy-5,6-O-(1-ethylpropylidene) hexene (I) in a first reaction mixture with ozone in a non-reactive organic solvent and removing a resulting product which contains D-2,2-difluoro-3,4,5-trihydroxy-4,5-O-1-ethylpropylidene)-pentaldehyde (II) from the organic solvent; reacting in a second reaction mixture the resulting product containing the pentaldehyde (II) with water to produce the pentopyranose (III) in the second reaction mixture; and separating the pentopyranose (III) from the second reaction mixture. From this reaction, there is obtained an excess of pentopyranose isomer III needed to produce 2'-deoxy-2',2'-difluorocytidine from which III may be easily isolated in pure form which was unexpected.

DETAILED DESCRIPTION AND PREFERRED EMBODIMENTS

The reaction to produce intermediate hexene (I) is preferentially performed in a non-reactive atmosphere. This atmosphere can be nitrogen, argon or the like. The reaction is also conducted in a non-reactive solvent, preferably tetrahydrofuran (THF). Other solvents are diethyl ether and ethylene glycol ethers, such as glyme.

The metal used to form the organometallic complex in producing intermediate hexene (I) is preferably zinc. Lithium can be used. Other metals are magnesium, cesium, lead, bismuth, indium, tin, cadmium and manganese.

The reaction temperatures and times to produce intermediate hexene (I) vary depending upon the organometallic complex. With zinc, the temperatures are preferably between about 0° and 50° C. for 1 to 70 hours. For lithium, the temperatures are preferably between about −90° C. to −100° C. for 5 to 60 minutes. Zinc is preferred because of the higher reaction temperatures and better yields.

An excess of the 3-bromo-3,3-difluoropropene may be used in the reaction to produce intermediate hexene (I). Preferably the amount of propene is between about 1.0 and 2.0 molar equivalents.

Water is added to the reaction mixture to hydrolyze the organometallic complex. The intermediate hexene (I) is then separated from the reaction mixture usually by extraction with an organic solvent which is not miscible with water, such as diethyl ether. The organic solvent is then removed, such as by distillation.

The reaction to form intermediate pentaldehyde (II) involves the use of ozone in an organic solvent which is inert to the reaction. The preferred solvent is methylene chloride. Other solvents are for instance halogenated hydrocarbons such as chloroform, esters such as ethyl acetate, and aromatic or aliphatic hydrocarbons such as benzene and hexane. The reaction is preferably conducted at between about −20° and +30° C.

The reaction to form pentopyranose (III) involves a hydrolysis reaction. An organic solvent, such as acetonitrile, preferably serves as a co-solvent for the reactants. The hydrolysis reaction is preferably conducted at between about 20° and 100° C.

It was unexpected that the reaction would favor pentopyranose (IIIA). This is a significant advantage in producing 2'-deoxy-2',2'-difluorocytidine.

In the following Examples, general NMR spectra were recorded on a Bruker AC 300 spectrometer ($^1$H NMR at 300 MHz, $^{19}$F NMR at 282 MHz, $^{13}$C NMR at 75 MHz). $^1$H NMR chemical shifts are reported in δ ppm relative to the solvent (acetone-$d_6$, 2.04 ppm; CDCl$_3$, 7.24 ppm; DMSO-$d_6$, 2.49 ppm). $^{19}$F NMR chemical shifts are reported in δ ppm relative to C$_6$F$_6$ (−162.9 ppm). $^{13}$C NMR chemical shifts are reported in δ ppm relative to the solvent (acetone-$d_6$, 29.8 ppm; CDCl$_3$, 77.0 ppm; DMSO-$d_6$, 39.5 ppm). Multiplicities are reported as s (singlet), brs (broad singlet), d (doublet), brd (broad doublet), t (triplet), dd (doublet of doublets), and dq (doublet of quartets). Flash chromatography was done on EM Science silica gel 60, 230–400 mesh, and TLC was performed on Merck glass-backed silica gel 60 plates, 0.25 mm thickness, with a 254 nm fluorescent indicator. Gas chromatography was performed on a HP5890 with a 30 m×0.1 mm ID DB1 capillary column with helium flow, a split injection, and flame ionization detection. The column temperature was 50° C. for 3 minutes, 15° C./minute to 250° C., and held there for 5 minutes. Melting points were determined using a Meltemp device and are uncorrected.

EXAMPLE 1

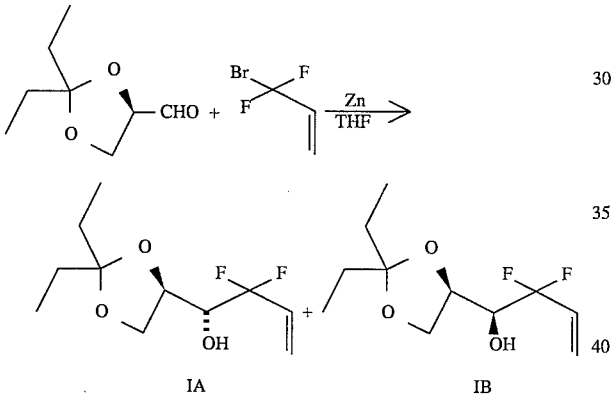

D-3,3-difluoro-4,5,6-trihydroxy-5,6-O-(1-ethylpropylidene)hexene (IA and IB)

A dry 250 mL round-bottomed flask fitted with a mechanical agitator, a reflux condenser, and a nitrogen purge was charged with 4.6 g zinc dust (70 mmol, 1.2 eq), 9.3 g freshly distilled D-glyceraldehyde pentanide (59 mmol), and 100 mL anhydrous THF. 3-Bromo-3,3-difluoropropene (6.6 mL, 65 mmol, 1.1 eq) was added and the slurry stirred under nitrogen at ambient temperature for three days. To the flask was added 100 mL ether, 40 mL of a 5% aqueous solution of sodium bicarbonate, and about 2 g filter aid. The slurry was filtered, the cake washed with ether and water, and the layers separated. The aqueous layer was extracted with 10 mL ether and the combined ether layers were washed with 20 mL water. The solution was dried over anhydrous sodium sulfate and concentrated in vacuo to give 13.8 g yellow oil. The product (IA and IB) was purified by taking a center cut from a vacuum distillation, bp 76°–81° C., 0.7 mm Hg. The yield of purified homoallylic alcohols was 5.7 g. The overall purity was 95% by GC and the erythro:threo ratio was 2.7:1 whereas it was 3.3:1 before distillation. The retention times on the GC were 12.96 minutes for threo (IB) and 13.16 minutes for erythro (IA).

Erythro (IA): $^1$H NMR (CDCl$_3$) 6.15 (m, 1H), 5.85 (d, J=16 Hz, 1H), 5.62 (d, J=11 Hz, 1H), 4.4 (m, 1H), 4.2 (m, 1H), 4.1 (m, 1H), 1.75 (m, 4H), 1.05 (m, 6H). $^{19}$F NMR (DMSO-$d_6$) −108.6 (d,t J=250 Hz, J=15 Hz), −111.5 (t, d J=250 Hz, J=12 Hz). $^{13}$C NMR (CDCl$_3$) 130.2 (t, J=25 Hz), 129.9 (t, J=25 Hz), 121.0 (t, J=10 Hz), 120.7 (q, J=240 Hz), 112.7, 74.3, 73.1 (t, J=30 Hz), 65.4, 29.4, 28.9, 8.1, 8.0. ms (EI) 207 (M-Et), 129, 57.

Threo (IB): $^1$H NMR (CDCl$_3$) 6.2 (m, 1H), 5.85 (d, J=16 Hz, 1H), 5.68 (d, J=12 Hz, 1H), 4.4 (m, 1H), 4.2 (m, 1H), 3.9 (m, 1H), 1.75 (m, 4H), 1.05 (m, 6H). $^{19}$F NMR (DMSO-$d_6$) −106.1 (d, t J=250 Hz, J=15 Hz), −111.3 (t, d J=250 Hz, J=12 Hz). $^{13}$C NMR (CDCl$_3$) 130.0 (t, J=25 Hz), 130.0 (t, J=25 Hz), 121.1 (t, J=10 Hz), 120.7 (q, J=240 Hz), 112.7, 74.2, 73.0 (t, J=30 Hz), 66.8, 29.5, 29.0, 8.1, 8.0, ms (EI) 207 (M-Et), 129, 57.

EXAMPLE 2

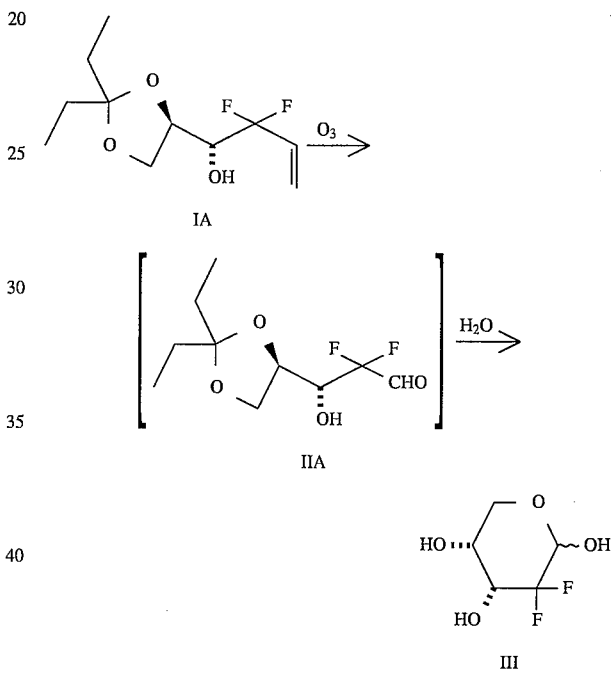

2-Deoxy-2,2-difluoro-β-D-ribo-pentopyranose (III)

The reaction is the same for both the erythro isomer (IA) and the threo isomer (IB). The 2.7:1 mixture of homoallylic alcohols (0.53 g, 2.2 mmol) with erythro isomer (IA) and threo isomer (IB) was dissolved in about 50 mL methylene chloride and the solution placed in a 50 mL round-bottomed three-necked flask fitted with a sparge line and a magnetic stirrer. The solution was stirred in an ice bath and a stream of 2% ozone in air was sparged into the solution until a blue color persisted. After purging excess ozone, 7 mL of a 7% aqueous solution of sodium thiosulfate was added. After 5 minutes, the phases were separated, the lower layer washed with 10 mL water, and dried over anhydrous sodium sulfate. Removal of the solvent in vacuo at ambient temperature afforded 0.31 g of a colorless oil. The NMR spectra of aldehyde II (including isomer IIA and a threo isomer IIB) was complicated by hydrate formation but gc/ms analysis as above (in which hydrate would crack in the injection port) indicated the presence of the two diastereomeric aldehydes (EI, 209, loss of Et), particularly the desired erythro isomer aldehyde (IIA). Acetonitrile (15 mL) and 1 mL water was added to the oil and the solution stirred at 53° C. overnight. The solution was evaporated under high vacuum to give 0.21 g of a colorless oil. Thin layer chromatography indicated two major isomers of pentopyranose (III), including pentopyranose isomer IIIA and a pentopyranose isomer IIIB, $R_F$ 0.2 and 0.3, when the silica was eluted with toluene:isopropyl alcohol, 5:1. Authentic pentopyranose isomer (IIIA) prepared as below eluted with an $R_F$ of 0.2. The isomers III were separated by flash chromatography on silica using the same solvent system to provide 40 mg of the pentopyranose isomer (IIIB) of compound (III) with $R_F$ 0.3 as a colorless oil and 100 mg of the pentopyranose isomer (IIIA), $R_F$ 0.2, which was chromatographically and spectroscopically identical with authentic pentopyranose isomer (IIIA).

EXAMPLE 3

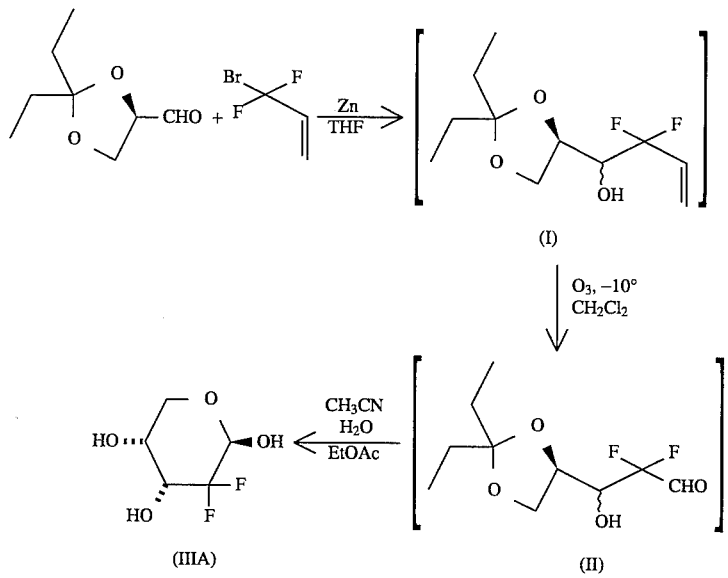

2-Deoxy-2,2-difluoro-β-D-ribo-pentopyranose (IIIA)

A dry 250 mL round-bottomed flask fitted with a mechanical agitator, a reflux condenser, and a nitrogen purge was charged with 4.6 g zinc dust (70 mmol, 1.2 eq), 9.3 g freshly distilled D-glyceraldehyde pentanide (59 mmol), and 100 mL anhydrous THF. 3-Bromo-3,3-difluoropropene (7.2 mL, 70 mmol, 1.2 eq) was added and the slurry stirred under nitrogen at ambient temperature for three days. To the flask was added 100 mL ether, 40 mL of a 10% aqueous solution of sodium bicarbonate, and about 4 g filter aid. The slurry was filtered, the cake washed with ether, and the layers separated. The aqueous layer was extracted with 10 mL ether and the combined ether layers were concentrated in vacuo to give a yellow oil which is D-3,3-difluoro-4,5,6-trihydroxy-5,6-O-(1-ethylpropylene)hexene (I). The oil was dissolved in about 100 mL methylene chloride and the solution placed in a 250 mL round-bottomed three-necked flask fitted with a sparge line and a magnetic stirrer. The solution was stirred in a bath of ice and acetone and a stream of 2% ozone in air was sparged into the solution until a faint blue color persisted. After purging excess ozone, 20 mL of a 7% aqueous solution of sodium thiosulfate and about 20 g solid sodium thiosulfate was added. After standing overnight, the solids were removed by filtration, the phases were separated, the aqueous layer was extracted with 20 mL methylene chloride, the combined organic layers washed with 20 mL saturated aqueous sodium bicarbonate, and the solvent was removed in vacuo to afford a colorless oil. Acetonitrile (100 mL) and water (10 mL) were added and the solution stirred overnight at 42° C. Part of the solvent was removed by distillation in vacuo and 100 mL acetonitrile and 10 mL water were added again. After stirring overnight at 48° C. and for 4 days at 39° C., the solvent was removed in vacuo. The residue was dissolved in 50 mL water and extracted with 20 mL ether. The aqueous layer was concentrated in vacuo and the residue extracted with 40 mL ethyl acetate at near reflux. The ethyl acetate solution was decanted away from an insoluble residue, concentrated to about half its volume, and cooled to ambient temperature. A seed crystal of the desired product was added and a slow stream of nitrogen was used to evaporate the ethyl acetate over two days until the volume was about 5 mL. The product was isolated by filtration, washed with 1 mL ethyl acetate, and dried in vacuo at 40° C. to give 1.09 g (11%) of white solid 2-Deoxy-2,2-difluoro-β-D-ribo-pentopyranose (IIIA), mp 129°–137° C. Its $^{19}F$ and $^1H$ NMR spectra were identical to that of authentic material and literature reports.

COMPARATIVE EXAMPLE 4

This Example shows the preparation of authentic pentopyranose (IIIA).

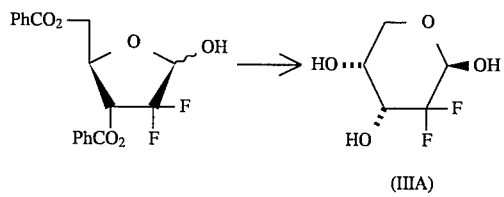

2-Deoxy-2,2-difluoro-β-D-ribo-pentopyranose (IIIA)

A 1-L three-necked flask equipped with thermometer, heating mantle, condenser and nitrogen inlet was charged with 97.85 g of 3,5-di-O-benzoyl-2-deoxy-2,2-difluoro-α- and β-D-ribo-pentofuranose (0.26 mol) and 500 mL of CH₃OH. To this mixture was added 53 mL of triethylamine (0.38 mol, 1.5 eq), and the solution was heated to 50° C. and stirred for 24 hours. The solution was then heated to reflux and 500 mL of CH₃OH was removed by distillation. Ethyl acetate was added and removed by distillation (four times, 250 mL each) until the distillation temperature reached 100° C. The mixture was stirred at ambient temperature for 15 hours, at 0° C. for 30 minutes, and then was filtered and washed with ether, producing 40.7 g of 2-Deoxy-2,2-difluoro-D-ribo-pentopyranose which had exclusively the β-configuration. Crude 2-Deoxy-2,2-difluoro-β-D-ribo-pentopyranose was recrystallized from ethyl acetate to afford 24.8 g of white solid IIIA (46% yield) having the following physical and spectral characteristics: $R_f$ 0.04, 0.12 (75 ethyl acetate: 50 heptane: 5 methanol); mp 137°–139° C.; $^1$H NMR (acetone-$d_6$) δ3.64 (1 H), 3.91 (1 H), 3.94 (1 H), 4.05 (1 H), 5.02 (1 H); $^{19}F$ NMR (acetone-$d_6$) δ –123.1 (brd, $J_{FF}$=253 Hz), –119.2 (dq, $J_{HF}$=3.7, 13.6 Hz, $J_{FF}$=250 Hz); $^{13}$C NMR (acetone-$d_6$) δ63.56, 68.55, 68.55, 91.89, 117.30.

Analysis for $C_5H_8O_4F_2$:

Calc.: C, 35.30; H, 4.74; F, 22.34; Found: C, 35.59; H, 4.74; F, 22.52.

It is intended that the foregoing description be only illustrative of the present invention and the present invention be limited only by the hereinafter appended claims.

I claim:

1. A process for the preparation of D-3,3-difluoro-4,5,6-trihydroxy-5,6-O-(1-ethylpropylidene)hexene (I) the improvement which comprises:

reacting in a reaction mixture an organometallic complex of 3-bromo-3,3-difluoropropene with D-glyceraldehyde pentanide in a non-reactive organic solvent until the hexene (I) is formed as erythro and threo isomers with a molar excess of the erythro isomer in the reaction mixture.

2. The process of claim 1 wherein the organic solvent is tetrahydrofuran and wherein the reaction is conducted for between about 1 and 70 hours at ambient temperatures with the organometallic complex of zinc and the 3-bromo-3,3-difluoropropene.

3. The process of claim 1 wherein in addition the hexene (I) is separated from the reaction mixture by adding water to the reaction mixture to hydrolyze the organometallic complex, the hexene (I) is extracted from the reaction mixture with diethyl ether and then the diethyl ether is removed to separate the hexene (I).

4. The process of claim 3 wherein in addition the separated hexene (I) is purified by vacuum distillation.

5. The process of claim 1 wherein the 3-bromo-3,3-difluoropropene is present in a molar excess.

6. The process of claim 1 wherein the organometallic complex is a zinc complex.

7. The process of claim 1 wherein the organometallic complex is a lithium complex.

8. The process of claim 1 wherein the organic solvent is tetrahydrofuran, and wherein the reaction is for between about 5 to 60 minutes with the organometallic complex of lithium with 3-bromo-3,3-difluoropropene.

9. A process for the preparation of 2-deoxy-2,2-difluoro-β-D-ribo-pentopyranose (IIIA) which comprises:

(a) reacting D-3,3-difluoro-4,5,6-trihydroxy-5,6-O-(1-ethylpropylidene)hexene (I) in a first reaction mixture with ozone in a non-reactive organic solvent and removing a resulting product which contains D-2,2-difluoro-3,4,5-trihydroxy-4,5-O-1-ethylpropylidene-)pentaldehyde (II) from the organic solvent;

(b) reacting in a second reaction mixture the resulting product containing the pentaldehyde (II) with water to produce the pentopyranose (IIIA) in the second reaction mixture; and (c) separating the pentopyranose (IIIA) from the second reaction mixture.

10. The process of claim 9 wherein hexene (I) is a mixture of erythro and threo isomers which is enriched in the erythro isomer.

11. The process of claim 9 wherein the organic solvent is methylene chloride.

12. The process of claim 9 wherein the hexene (I) is prepared by reacting 3-bromo-3,3-difluoropropene with D-glyceraldehyde in a non-reactive organic-solvent.

13. The process of claim 12 wherein the hexene (I) is a mixture of erythro and threo isomers with a molar excess of the erythro isomer.

14. The process of claim 13 wherein the organic solvent is tetrahydrofuran and wherein the reaction is conducted for between about 1 and 70 hours at ambient temperatures with the organo metallic complex of zinc and the 3-bromo-3,3-difluoropropene.

15. D-3,3-difluoro-4,5,6-trihydroxy-5,6-O- (1-ethylpropylidene)hexene (I).

16. Erythro-D-3,3-difluoro-4,5,6-trihydroxy-5,6-O-(1-ethylpropylene)hexene (IA).

17. D-2,2-difluoro-3,4,5-trihydroxy-4,5-O-(1-ethylpropylidene)pentaldehyde (II).

18. Erythro-D-2,2-difluoro-3,4,5-trihydroxy-4,5-O-(1-ethylpropylidene)pentaldehyde (IIA).

19. A process for the preparation of 2-deoxy-2,2-difluoro-β-D-ribo-pentopyranose (IIIA) which comprises:

(a) reacting in a first reaction mixture an organometallic complex of 3-bromo-3,3-difluoropropene with D-glyceraldehyde pentanide in a non-reactive organic solvent until D-3,3-difluoro-4,5,6-trihydroxy-5,6-O-(1-ethylpropylidene)hexene (I) is formed;

(b) reacting in a second reaction mixture the resulting D-3,3-difluoro-4,5,6-trihydroxy-5,6-O-(1-ethylpropylidene)hexene (I) with ozone in a non-reactive organic solvent and removing a resulting product which contains D-2,2-difluoro-3,4,5-trihydroxy-4,5-O-1-ethylpropylidene)pentaldehyde (II) from the organic solvent;

(c) reacting in a third reaction mixture the resulting product containing the pentaldehyde (II) with water to produce the pentopyranose (IIIA); and (d) separating the pentopyranose (IIIA) from the third reaction mixture.

* * * * *